United States Patent [19]
Dumoulin

[11] Patent Number: 5,277,192
[45] Date of Patent: Jan. 11, 1994

[54] IMAGING OF TURBULENCE WITH MAGNETIC RESONANCE

[75] Inventor: Charles L Dumoulin, Ballston Lake, N.Y.

[73] Assignee: General Electric Company, Schenectady, N.Y.

[21] Appl. No.: 946,702

[22] Filed: Sep. 18, 1992

[51] Int. Cl.$^5$ .............................. A61B 5/055
[52] U.S. Cl. ................. 128/653.3; 128/708; 324/306; 324/309; 324/312
[58] Field of Search ............... 128/653.2, 653.3, 708; 324/306, 309, 312

[56] References Cited

U.S. PATENT DOCUMENTS

| | | | |
|---|---|---|---|
| 4,602,641 | 7/1986 | Feinberg | 128/653.3 |
| 4,683,431 | 7/1987 | Pattany et al. | 128/653.3 |
| 4,796,635 | 1/1989 | Dumoulin | 128/653.3 |
| 5,133,357 | 7/1992 | Dumoulin et al. | 128/653.3 |

*Primary Examiner*—Ruth S. Smith

[57] ABSTRACT

Turbulent fluid flow within a subject is imaged using a magnetic resonance imaging method which is sensitive to non-coherent changes in the magnetic resonance signal intensity and phase. Flow-induced phase shifts are generated in the magnetic resonance signal with a bi-polar magnetic field gradient pulse applied in an arbitrary orientation. Data is acquired in the presence of a uniform flow encoding field gradient applied in an selected direction independent of the bi-polar field gradient pulse. The flow encoding gradient induces a frequency shift in the data which is proportional to position along the direction of the gradient. The spatial distribution of magnetic resonance spins within the flowing fluids along this applied frequency-encoding magnetic field gradient is determined by Fourier transformation. Data acquisition and Fourier transformation are repeated for a plurality of cardiac cycles of the subject and the standard deviation of the magnetic resonance signal at each position along the applied magnetic field gradient is calculated to produce a one-dimensional projection of the random component of the flow-induced phase shift. The steps of data acquisition, Fourier transformation and standard deviation calculation are then repeated for multiple directions of the frequency-encoding magnetic field gradient. A two-dimensional spatial distribution of the non-coherent component of the magnetic resonance signal is then determined by projection reconstruction of the standard deviation projection data sets.

7 Claims, 5 Drawing Sheets

IMAGING OF TURBULENCE WITH MAGNETIC RESONANCE

BACKGROUND OF THE INVENTION

1. Field of the Invention

The present invention relates to the field of magnetic resonance imaging and more specifically to the field of imaging flowing fluids with magnetic resonance within a subject.

2. Description of Related Art

In magnetic resonance (MR) imaging of a subject, complex fluid flow within, particularly those which vary with time, is the source of artifacts. Methods of minimizing these artifacts include the use of cardiac gating, flow-compensated gradient waveforms and short MR echo times. These methods extract a coherent signal from the acquired MR signals, discarding non-coherent MR signals. Nevertheless, the non-coherent portion of the signal contains useful diagnostic information.

The physiological processes which result in non-coherent MR signals are of great interest clinically, but are very difficult to measure non-invasively. Complex fluid flow, such as turbulence, has been observed in the descending aortas of dogs using hot-film anemometer methods in which upstream blood is heated and its passage observed downstream. This method requires the placement of two catheters, and consequently is highly invasive. It has only been performed in humans undergoing diagnostic X-ray angiographic procedures. The angiography studies suggest that some level of turbulence is present in almost all individuals over the age of forty, and the degree of turbulence increases with both age and the stiffness of the arterial system.

Aside from its invasive nature, another limitation of the hot-film technique is that no imaging information is obtained, since the catheters are point source detectors and their exact radial placement in the vessel is not usually well known.

Currently, there is a need to measure complex fluid flow by non-invasive methods.

SUMMARY OF THE INVENTION

The method of the present invention provides MR images of flowing fluids in a subject by employing a cardiac gated, flow-encoded projection reconstruction technique. With this method, a subject is placed in a substantially homogeneous magnetic field. The subject's cardiac EKG wave is monitored, and upon detection of systole, a magnetic resonance (MR) pulse sequence is initiated. In this sequence a slab selective rf excitation pulse at the Larmor frequency is applied in conjunction with an applied magnetic field gradient to cause resonant nuclei, known as "spins", in a selected slab within the subject to be nutated into a transverse plane. A bi-polar flow-encoding magnetic field gradient is then applied to induce a phase shift in a MR signal responsive to motion of the resonant spins in the direction of the flow-encoding gradient. An MR signal is acquired in the presence of another magnetic field gradient which is applied in a direction independent of the slab-selective and flow-encoding gradients. Acquisition of the MR signal in the presence of this gradient causes the position of each moving fluid to be encoded according to frequency in the MR signal. The data is then Fourier transformed to obtain fluid velocity vs. position along an axis in the direction of the readout gradient.

The steps of applying a slab selective rf pulse, flow-encoding gradient, frequency encoding gradient and data acquisition are repeated a plurality of repetitions during a single cardiac cycle of the subject. These steps are then repeated in the same fashion across a plurality of cardiac cycles. Signals arising from stationary tissue and fluid moving in a constant fashion will be very similar for a specific time in the cardiac cycle for a specific location. Signals arising from fluid having random components of motion, however, will be different. This randomness is measured by calculating the standard deviation of the N signal acquisitions.

Signal acquisition is repeated for a plurality of M orientations of the flow encoding gradient. The standard deviation calculation is repeated for each orientation to result in M one-dimensional projections of the random component of the magnetic resonance signal. A two-dimensional distribution of these random components is then calculated by applying a projection reconstruction to the one-dimensional projections.

OBJECTS OF THE INVENTION

It is an object of the present invention to provide a system for obtaining images of the non-constant components of motion of fluids within a subject.

It is another object of the present invention to provide a system for obtaining images of turbulent fluid flow within a subject.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

FIG. 1a is a sequencing diagram of the radio-frequency and magnetic field gradient pulses in a presently preferred embodiment of the invention.

FIG. 1b is a flow vs. position diagram reconstructed from the signals of FIG. 1a.

DETAILED DESCRIPTION OF THE INVENTION

In the present invention a subject is placed in a substantially homogeneous magnetic field generated by the magnet of a magnetic resonance (MR) imaging system to cause nuclear spins to obtain longitudinal spin magnetization in manner well know to those skilled in the art of MR imaging. Radio-frequency and magnetic field gradient pulses are then applied and MR response signals detected. MR flow imaging is described in U.S. Pat. No. 5,133,357 QUANTITATIVE MEASUREMENT OF BLOOD FLOW USING CYLINDRICALLY LOCALIZED FOURIER VELOCITY ENCODING by Charles L. Dumoulin, Christopher J. Hardy, S. P. Souza and Steven A. Ash issued Jul. 28, 1992, assigned to the present assignee and hereby incorporated by reference.

Figure 1:
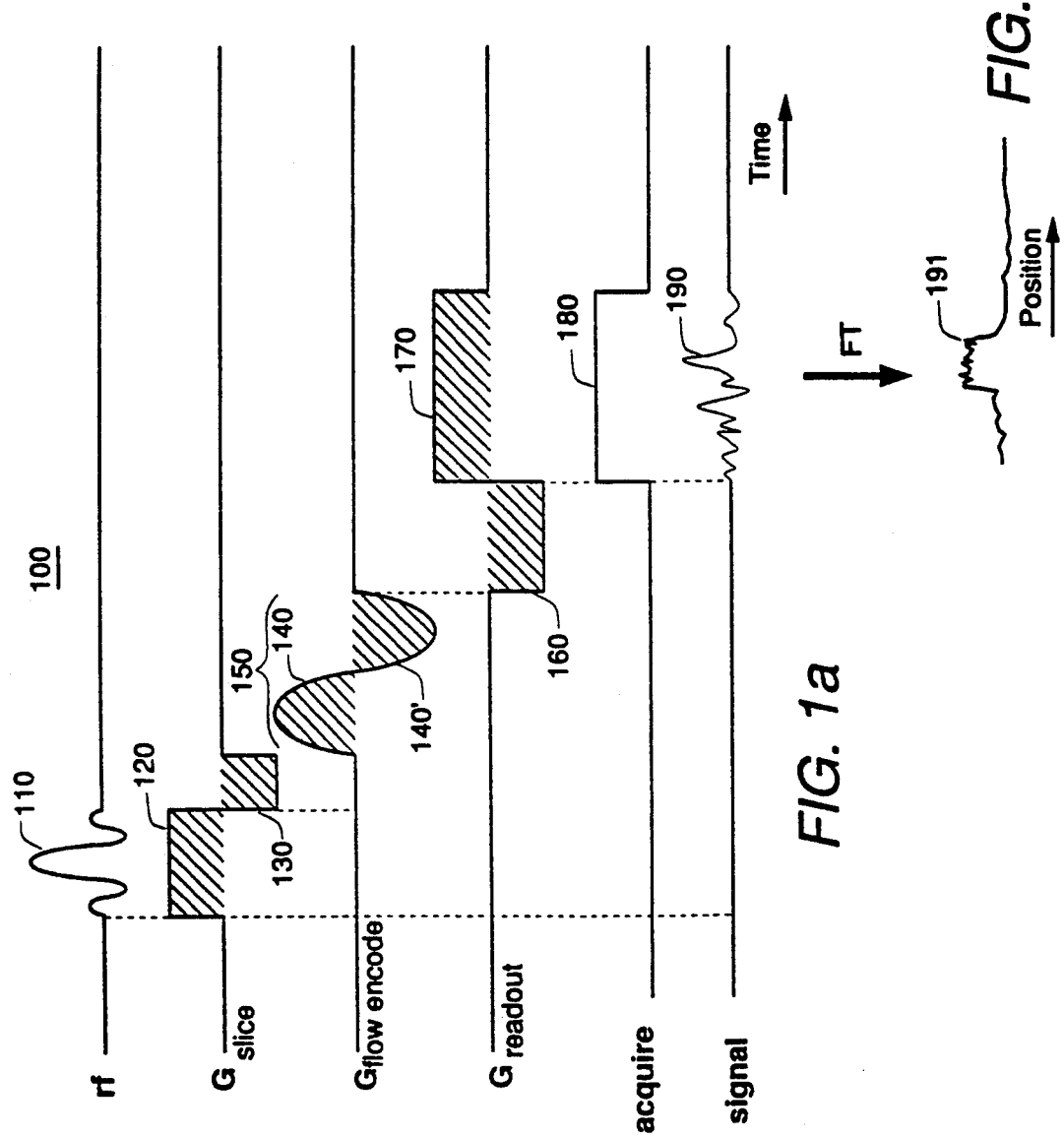

FIG. 1 illustrates a pulse sequence 100 employed by the present invention. Pulse sequence 100 is comprised of a slab selective rf pulse 110 which is applied to a subject to be imaged simultaneously with the application of a substantially uniform slab selective magnetic field gradient pulse 120 of selected amplitude. RF pulse 110 and field gradient pulse 120 nutate a selected ensemble of nuclear spins within the subject into a transverse plane. This selected ensemble has a spatial distribution which is ideally limited to a slab of predetermined thickness. After the application of rf pulse 110 and gradient pulse 120 the nutated spins within the slab will have different phase shifts. Substantially all of the spins in the ensemble will return to a common phase shift by the application of a slab refocusing magnetic field gradient pulse 130. In the present embodiment of the invention, the product of the amplitude and duration of field gradient pulse 120 is substantially twice that of slab refocusing field gradient 130.

At a selected time after the application of slab selective gradient pulse 120, a flow encoding magnetic field gradient pulse 150 is applied in a direction independent of the slab selective gradient pulse 120 and slab refocusing gradient pulse 130. Flow encoding pulse 150 is comprised of two lobes: a first lobe 140 having a selected product of amplitude and duration, and a second lobe 140' having an amplitude-duration product substantially equal, but of opposite polarity, to that of the first lobe 140. Flow encoding pulse 150 can be applied simultaneously with slab refocusing pulse 130 if desired.

In the present embodiment of the invention, flow-encoding gradient pulse 150 is bi-polar. A bi-polar gradient pulse induces a phase shift in transverse spin magnetization which is proportional to velocity and higher orders of motion. This allows moving spins to be differentiated from stationary spins. The moving spins are described by:

$$\text{motion} = \frac{d^k x}{dt^k} \geq 0, k \geq 1, \quad (1)$$

where x is the displacement along the flow encoding magnetic field gradient pulse direction. Flow-encoding pulses which incorporate three or more lobes can be designed to induced phase shifts in transverse spin magnetization which are proportional to selected orders of motion described by:

$$\text{motion} = \frac{d^k x}{dt^k} \geq 0, k \geq 2. \quad (2)$$

This flow-encoding pulse allows imaging of spins having non-constant velocity. Flow encoding methods are described in the above mentioned U.S. Pat. No. 5,133,357.

After the application of flow-encoding pulse 150, a readout dephasing magnetic field gradient pulse 160 is applied at a projection angle $\theta_m$ substantially orthogonal to slab selective gradient pulse 120 and slab refocusing pulse 130. Readout dephasing pulse 160 induces a phase shift in transverse spin magnetization which is proportional to the spin's position along the direction of readout dephasing pulse 160. A readout magnetic field gradient pulse 170 is then applied in the same direction as readout dephasing gradient pulse 160, but with opposite polarity. In the present embodiment of the invention, readout gradient pulse 170 has a time-amplitude product which is twice that of the time amplitude product of readout dephasing lobe 160.

Simultaneous with the application of readout gradient pulse 170, a data acquire signal 180 is propagated within the MR imaging system, causing the system to acquire MR signal 190 from the subject. Since MR signal 190 is acquired simultaneously with readout gradient pulse 170, signal 190 is composed of an ensemble of signals, each at a frequency proportional to the position of a signal-generating spin.

In FIG. 1b, a transformed MR set 191 of fluid velocity vs. position along the direction of readout gradient pulse 170 is obtained by calculating the Fourier transformation of MR signal 190. Transformed MR set 191 is stored for further processing.

Figure 2:
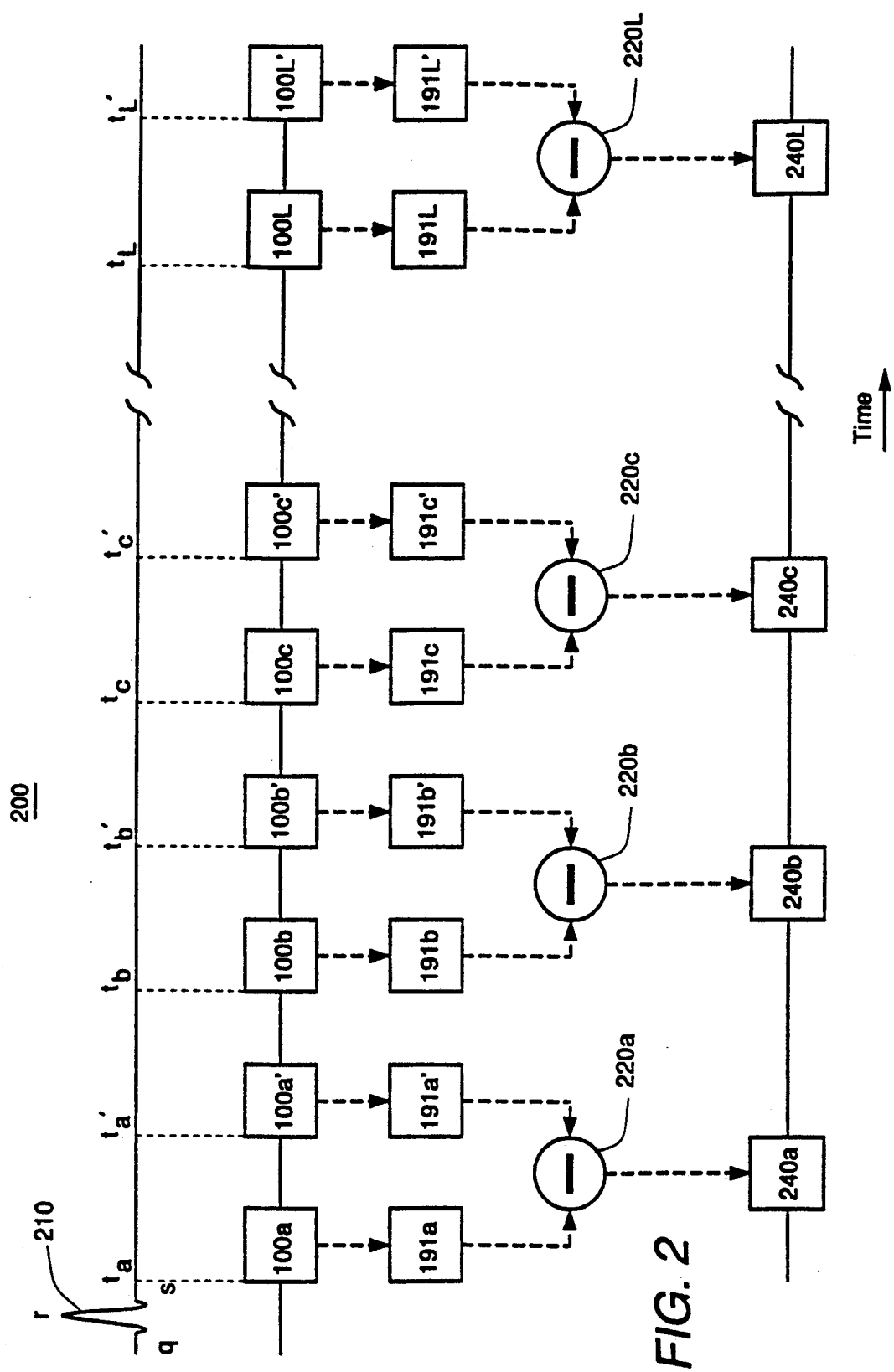
FIG. 2 is a sequencing diagram illustrating the application of the radio-frequency and magnetic field gradient pulse sequences at different points during the subject's cardiac cycle.

FIG. 2 is a timing diagram illustrating one embodiment of the invention in which pulse sequence 100 of FIG. 1 is initiated a plurality $2 \times L$ times for a given orientation angle at a specific time period delay $t_a$, $t_a'$, $t_b$, $t_b'$, $t_c$, $t_c'$ . . . $t_L$, $t_L'$, respectively after detection of a cardiac trigger event. In the present embodiment, the system searches for a waveform in the subject's electrocardiograph which represents a heartbeat of the subject. This waveform is known as a qrs complex 210. A first pair of pulse sequences 100a, 100a' is performed at a time delay of $t_a$, $t_a'$ respectively, after a cardiac trigger event, such as qrs complex 210. The MR signals 190 from each sequence is converted to digital form and Fourier transformed to create transformed MR sets 191a, 191a', and a difference is calculated between the transformed MR sets in a subtraction step 220a. The resulting difference data forms a first frame of data 240a. A second pair of pulse sequences 100b, 100b' are then applied at a time delay of $t_b$, $t_b'$, respectively, after a cardiac trigger event, followed by digitizing and Fourier transforming the MR signals to result in MR sets 191b, 191b' and then subtracting them in step 220b to generate a second frame of data 240b. Likewise, a third pair of sequences 100c, 100c' are applied, followed by a third subtraction step 220c to form a third frame of data 240c. The steps are repeated until a last pair of pulse sequences 100L, 100L' are applied, followed by the application of a subtraction step 220L to generate a last frame of data 240L. Frames 240a, 240b . . . 240L represent changes in velocity vs. position for a number of time periods in a single cardiac cycle, for a single projection angle $\theta_m$.

Alternatively, pulse sequence 100 of FIG. 1 may be applied responsive to more than one cardiac trigger event.

Frames 240a, 240b, . . . 240L are then collected and stored for a plurality of N cardiac cycles, resulting in N*L frames. Each frame represents non-constant flow values at a plurality of locations $x_1$, $x_2$, $x_3$, . . . $x_n$ along an axis in the direction of projection angle $\theta_m$.

The standard deviation of each flow value at a location $x_i$ for a projection angle $\theta_m$ across a plurality of cardiac cycles N is calculated for each location $x_i$ to determine a projection set $p_m$.

Figure 3:
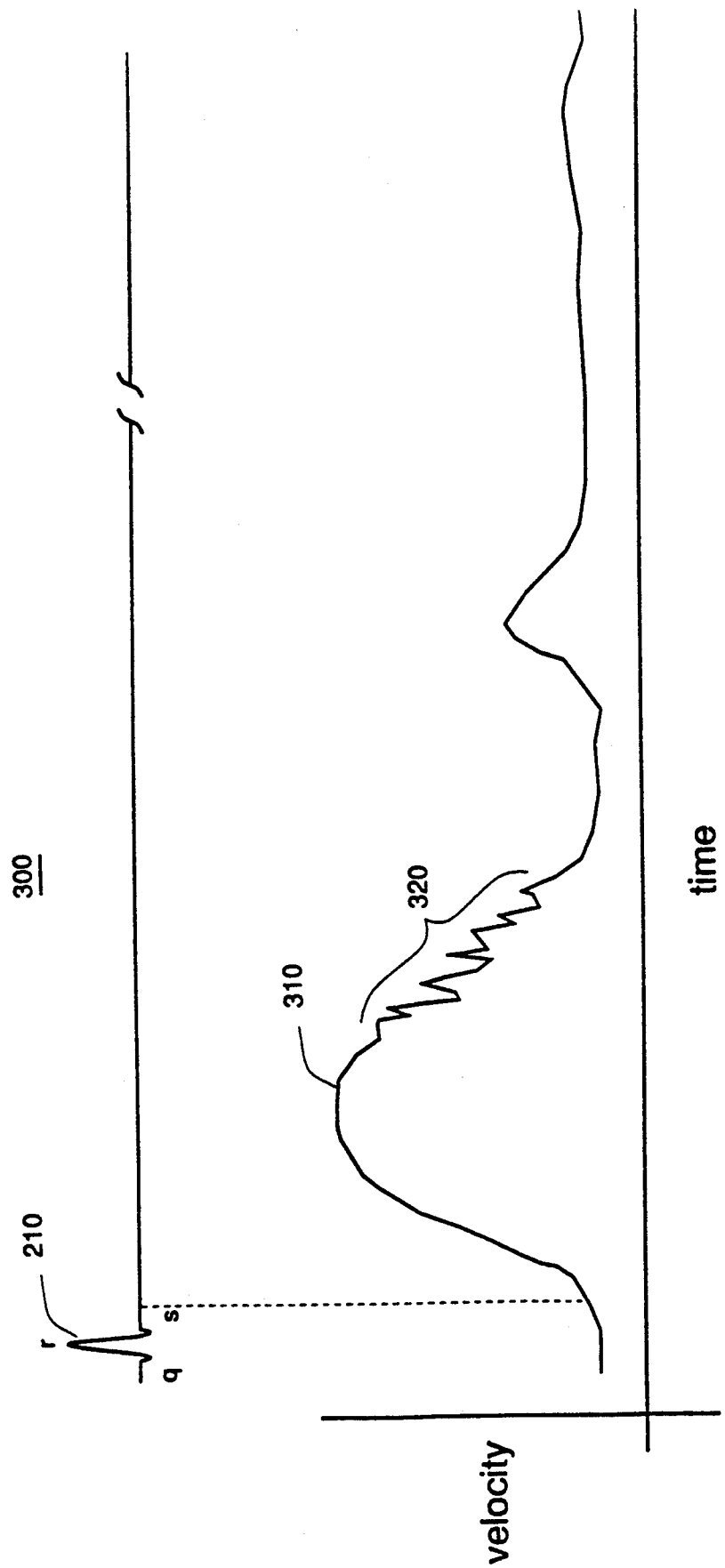
FIG. 3 is a velocity vs. time diagram of blood flow in a vessel experiencing turbulent flow during a portion of the cardiac cycle.

Transformed MR sets 191a, 191a', 191b, 191b', 191c, 191c', ... 191L, 191L' may be rearranged to produce a velocity vs. time diagram during a cardiac cycle as shown in FIG. 3. Two components are present in this response curve: a stable component 310 which is consistent from cardiac cycle to cardiac cycle and a random component 320 which is not consistent from cardiac cycle to cardiac cycle. Random component 320 arises from complex fluid motion such as turbulence and is typically, but not always, limited to a selected portion of the subject's cardiac cycle. This turbulence may be indicative of vascular diseases and used as a factor in diagnosis.

Figure 4A:
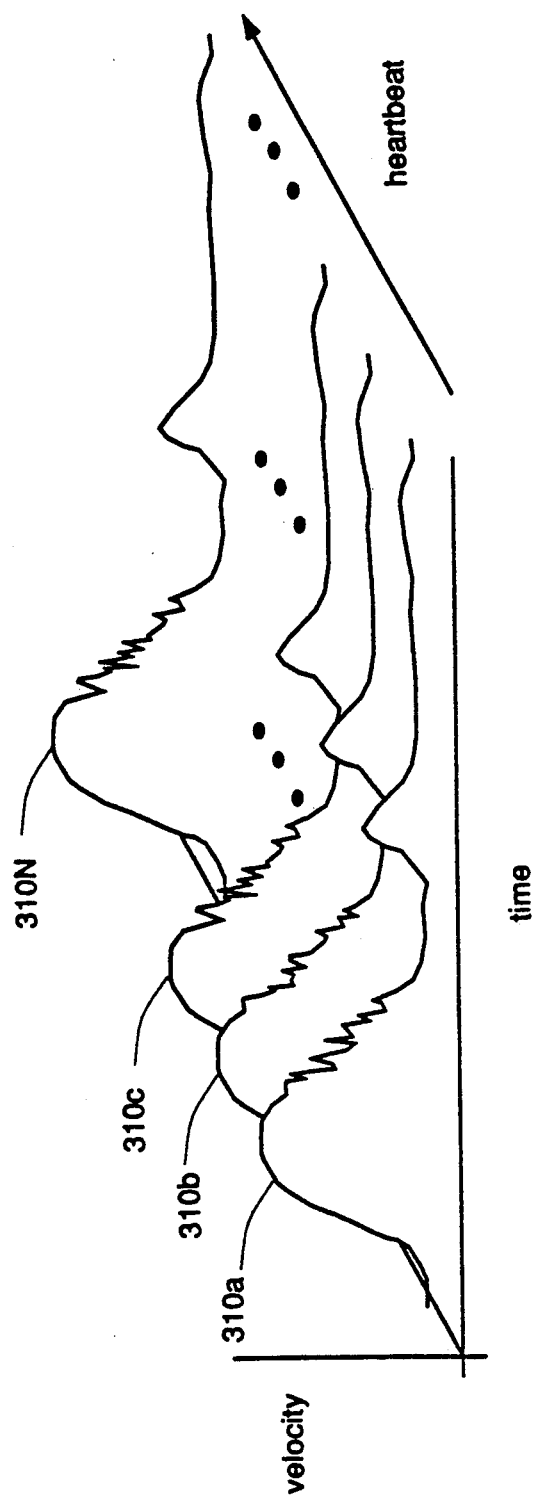
FIG. 4a is a plurality of velocity vs. time diagrams of blood flow in a vessel each corresponding to a different cardiac cycle of the subject.
Figure 4B:
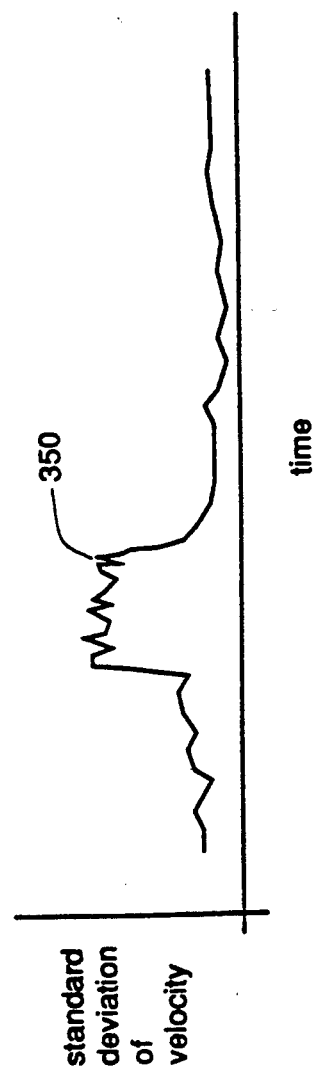
FIG. 4b is a standard deviation vs. time diagram of the blood velocity in a vessel for several cardiac cycles.

Velocity vs. time diagrams 300 of FIG. 3 for a single location over a plurality of N cardiac cycles are shown in FIG. 4a. In these diagrams portions 310a, 310b, 310c ... 310N of the diagrams are roughly identical for each cardiac cycle, but differ somewhat due to random turbulence. One measure of the randomness in the velocity vs. time diagrams is the standard deviation of the velocity. Other statistical deviation measurements may be used. The standard deviation is calculated across cardiac cycles for each specific point in time to result in FIG. 4b. FIG. 4b shows a standard deviation vs. time response curve 350 derived from the data shown in FIG. 4a.

The pulse sequences of FIGS. 1 and 2 are repeated a plurality M times, each at a different projection angle $\theta_m$, m = 1,2,3, ... M. Each projection set $p_m$ is obtained with readout dephasing magnetic field gradient 160 and readout field gradient 170 having a unique projection angle $\theta_m$ which is substantially orthogonal to the slab selective field gradient. For a selected instant within the cardiac cycle, there are M projection sets $p_m$. These projection sets are backprojected to produce a two-dimensional image of fluid moving at a non-constant velocity.

Figure 5:
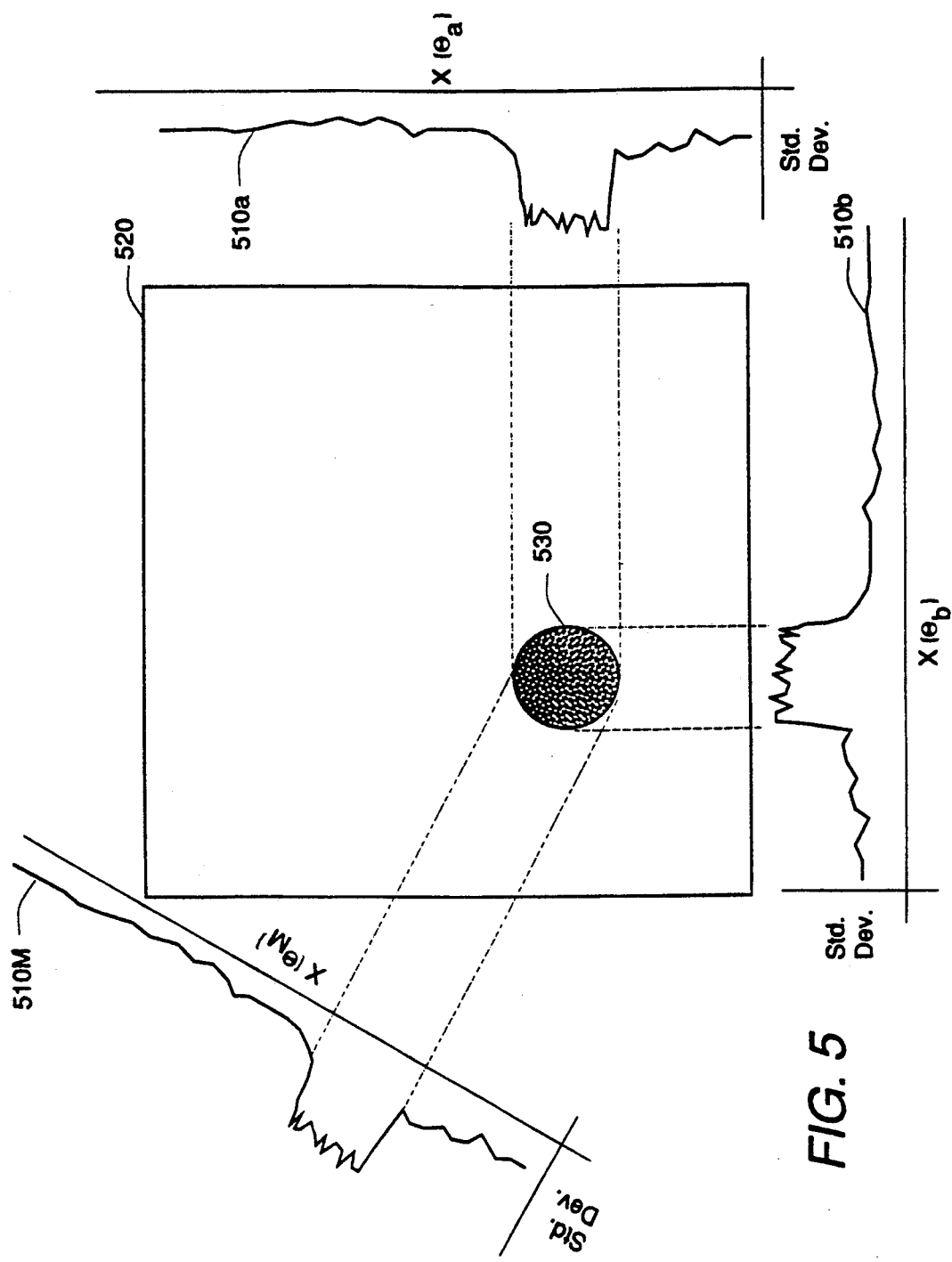
FIG. 5 is a spatial back projection reconstruction diagram illustrating the use of projection reconstruction to generate a two-dimensional image from a series of one-dimensional projections.

In FIG. 5, a plurality of projection sets are shown. A first projection set 510a was obtained from the statistical deviation of the frames of data acquired at a projection angle $\theta_m$ for a specific period in the cardiac cycle across a plurality of cardiac cycles. A second projection 510b was obtained with a different selected orientation. Other projections were obtained until a last projection 510M was acquired. The two-dimensional distribution 530 of random motion within the subject is then calculated by back-projection of projections 510a, 510b ... 510M to create an image 520 in a manner well know to those skilled in the art of projection tomography. Resulting image 520 is then displayed on a suitable display device such as a video display monitor for diagnostic purposes.

In an alternative embodiment of the invention, a plurality of MR signals 190 of FIG. 1 are obtained from repeatedly applying pulses 100. The MR signals are digitized and Fourier transformed but the subtraction steps shown in FIG. 2 are not performed. One or more frames of data are collected for each projection angle $\theta_m$. A statistics variation set is created by statistical analysis of the frames for a projection angle to determine where turbulence occurs. The projection sets are backprojected to create a two-dimensional spatial representation of turbulence.

While several presently preferred embodiments of the novel turbulence imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A method for obtaining magnetic resonance (MR) images of turbulence of fluid within a subject situated in a substantially homogeneous magnetic field comprising the steps of:
   a) applying a slice-selective MR excitation pulse to excite a slice of said subject;
   b) applying a flow-encoding magnetic field gradient pulse to the excited slice;
   c) applying a readout magnetic field gradient pulse to the excited slice at a selected projection angle $\theta_m$ m = 1,2,3, ... M where M represents a total number of projection angles;
   d) collecting an MR signal from said subject responsive to the MR excitation and magnetic field gradient pulses;
   e) Fourier transforming the MR signal to result in a set of flow velocity values for each position $x_i$ along an axis in a direction of the selected projection angle;
   f) repeating steps "a"–"e" during a single cardiac cycle of said subject to obtain a plurality of sets of flow velocity values;
   g) repeating steps "a"–"f" for a plurality of N cardiac cycles of said subject to obtain N sets of sets of flow velocity values; and
   h) producing a projection $p_m$ being a turbulence vs. position image of fluid within said subject by determining the standard deviation of the sets of flow velocity values for each position $x_i$ of the projection angle $\theta_m$.

2. The method for obtaining MR images as recited in claim 1 further comprising the steps of:
   a) repeating the steps "a"–"h" a plurality M repetitions to arrive at a plurality of M projections $p_m$, each repetition having the readout magnetic field gradient pulse oriented at a different projection angle $\theta_m$, m = 1,2,3, ... M; and
   b) back projecting the M projections $p_m$ to arrive at a two-dimensional image of fluid turbulence.

3. The method for obtaining MR images as recited in claim 1 in which the flow-encoding magnetic field gradient pulse is a bi-polar pulse.

4. The method for obtaining MR images as recited in claim 1 wherein the flow-encoding magnetic field gradient pulse has more than two lobes and images fluid having motion described by:

$$\text{motion} = \frac{d^k x_1}{dt^k} \text{ and } k \geq 2,$$

where $x_i$ is the displacement along the readout magnetic field gradient pulse direction.

5. The method for obtaining MR images as recited in claim 1 wherein steps "a"–"h" are initiated after detection of a cardiac trigger event in said subject.

6. A method for obtaining magnetic resonance (MR) images of turbulence of fluid within a subject situated in a substantially homogeneous magnetic field comprising the steps of:
   a) applying a slice-selective MR excitation pulse to excite a slice of said subject;

b) applying a flow-encoding magnetic field gradient pulse to the excited slice;
c) applying a readout magnetic field gradient pulse to the excited slice at a selected projection angle $\theta_m$;
d) collecting a first MR signal from said subject responsive to the rf pulse and magnetic field gradients;
e) Fourier transforming the first MR signal to result in a first set of flow velocity values for each position $x_i$ along an axis in a direction of the selected projection angle;
f) repeating steps "a"–"c";
g) collecting a second MR signal from said subject responsive to the rf pulse and magnetic field gradients;
h) Fourier transforming the second MR signal to result in a second set of flow velocity values;
i) subtracting the first set of flow velocity values from the second set of flow velocity values to obtain a motion encoded signal;
j) repeating steps "a"–"i" during a single cardiac cycle of said subject to obtain a plurality of motion encoded signals; and
k) repeating steps "a"–"j" for a plurality of N cardiac cycles of said subject to obtain N sets of motion encoded signals; and
l) producing a projection $p_m$ being a turbulence vs. position image of fluid within said subject having a zero average magnitude by determining the standard deviation of the motion encoded signals for each position $x_i$ of the projection angle $\theta_m$.

7. The method for obtaining MR images as recited in claim 6 further comprising the steps of:
a) repeating the steps "a"–"l" a plurality M repetitions to arrive at a plurality of M projections $p_m$, each repetition having the readout magnetic field gradient pulse oriented at a different projection angle $\theta_m$, m = 1,2,3, . . . M; and
b) back projecting the M projections $p_m$ to arrive at a two-dimensional image of fluid turbulence.

* * * * *